US006986835B2

(12) United States Patent
Balisky et al.

(10) Patent No.: US 6,986,835 B2
(45) Date of Patent: Jan. 17, 2006

(54) APPARATUS FOR PLATING SOLUTION ANALYSIS

(75) Inventors: Todd Alan Balisky, Corona, CA (US); Donald A. Cameron, Claremont, CA (US); Zhi-Wen Sun, San Jose, CA (US)

(73) Assignee: Applied Materials Inc., Santa Clara, CA (US)

( * ) Notice: Subject to any disclaimer, the term of this patent is extended or adjusted under 35 U.S.C. 154(b) by 521 days.

(21) Appl. No.: 10/287,901

(22) Filed: Nov. 4, 2002

(65) Prior Publication Data

US 2004/0084327 A1   May 6, 2004

(51) Int. Cl.
 *G01N 27/403*   (2006.01)
(52) U.S. Cl. .................................. 204/434; 204/409
(58) Field of Classification Search ............ 204/400, 204/409, 434; 205/775
 See application file for complete search history.

(56) References Cited

U.S. PATENT DOCUMENTS

| | | | | |
|---|---|---|---|---|
| 3,972,792 | A | * | 8/1976 | Laxen ..................... 204/409 |
| 4,102,770 | A | | 7/1978 | Moriarty et al. |
| 4,129,479 | A | * | 12/1978 | Morrow .................... 205/780 |
| 4,252,027 | A | | 2/1981 | Ogden et al. |
| 4,252,617 | A | * | 2/1981 | Heusler et al. .......... 205/793.5 |
| 4,286,965 | A | | 9/1981 | Vanhumbeeck et al. |
| 4,302,314 | A | * | 11/1981 | Golimowski et al. ....... 204/434 |
| RE31,694 | E | | 10/1984 | Slominski et al. |
| 4,528,158 | A | | 7/1985 | Gilles et al. |
| 4,595,462 | A | | 6/1986 | Vangaever et al. |
| 4,631,116 | A | | 12/1986 | Ludwig |
| 4,750,977 | A | | 6/1988 | Marrese |
| 4,774,101 | A | | 9/1988 | Harris et al. |
| 4,932,518 | A | | 6/1990 | Bernards et al. |
| 5,298,129 | A | | 3/1994 | Eliash |
| 5,298,132 | A | | 3/1994 | Reddy et al. |
| 5,389,546 | A | | 2/1995 | Becket |
| 5,391,271 | A | | 2/1995 | Ludwig |
| 5,450,870 | A | | 9/1995 | Suga et al. |
| 6,017,427 | A | | 1/2000 | Yamamoto |
| 6,365,033 | B1 | | 4/2002 | Graham et al. |
| 6,391,209 | B1 | | 5/2002 | Belongia et al. |
| 6,458,262 | B1 | | 10/2002 | Reid |
| 6,471,845 | B1 | | 10/2002 | Dukovic et al. |
| 6,495,453 | B1 | | 12/2002 | Brongersma et al. |
| 6,551,479 | B1 | | 4/2003 | Graham et al. |
| 6,592,736 | B2 | | 7/2003 | Fulton et al. |
| 6,596,148 | B1 | | 7/2003 | Belongia et al. |
| 6,635,157 | B2 | | 10/2003 | Dordi et al. |

* cited by examiner

*Primary Examiner*—Kaj K. Olsen
(74) *Attorney, Agent, or Firm*—Patterson & Sheridan

(57) ABSTRACT

A method and apparatus for analyzing plating solutions. The apparatus generally includes a plating cell, a reference electrolyte input, one or more external additive pumps, and a process controller. In one embodiment, the plating cell includes a cavity therein having a larger volumetric portion adjacent a smaller volumetric portion adapted to hold one or more solutions therein. The plating cell also includes a base disposed adjacent the bottom of the plating cell and adapted to receive and mix one or more test solutions as part of the plating solution analysis. In one configuration, the base includes electrical ports adapted to connect stimulation signals to a working electrode, counter electrode, and reference electrode disposed within the cell. The base also includes a thermal sensor in thermal contact with test solutions contained within the vessel.

25 Claims, 6 Drawing Sheets

APPARATUS FOR PLATING SOLUTION ANALYSIS

BACKGROUND OF THE INVENTION

1. Field of the Invention

Embodiments of the invention generally relate to an apparatus and method for conducting chemical analysis of substrate plating solutions.

2. Description of the Related Art

Metallization of sub-quarter micron sized features is a foundational technology for present and future generations of integrated circuit manufacturing processes. More particularly, in devices such as ultra large scale integration-type of devices, i.e., devices having integrated circuits with more than a million logic gates, the multilevel interconnects that lie at the heart of these devices are generally formed by filling high aspect ratio interconnect features with a conductive material, such as copper or aluminum, for example. Conventionally, deposition techniques such as chemical vapor deposition (CVD) and physical vapor deposition (PVD) have been used to fill interconnect features. However, as interconnect sizes decrease and aspect ratios increase, efficient void-free interconnect feature fill by conventional deposition techniques becomes increasingly difficult. As a result thereof, plating techniques, such as electrochemical plating (ECP) and electroless plating, for example, have emerged as viable processes for filling sub-quarter micron sized high aspect ratio interconnect features in integrated circuit manufacturing processes.

In an ECP process, for example, sub-quarter micron sized high aspect ratio features formed into the surface of a substrate may be efficiently filled with a conductive material, such as copper. ECP plating processes are generally two stage processes, wherein a seed layer is first formed over the surface and features of the substrate, and then the surface and features of the substrate are exposed to a plating solution, while an electrical bias is simultaneously applied between the substrate and an anode positioned within the plating solution. The plating solution is generally rich in ions to be plated onto the surface of the substrate, and therefore, the application of the electrical bias causes these ions to be reduced and thereby plated onto the seed layer. Furthermore, the plating solution generally contains organic additives, such as, for example, levelers, suppressors, and accelerators configured to control the plating distribution throughout the plating process. These additives are generally maintained within narrow tolerances, so that the repeatability of the plating operation may be maintained.

Conventional ECP systems generally utilize a cyclic voltammetric stripping (CVS) process to determine the organic additive concentrations in the plating solution. More particularly, three electrodes, a working electrode, a counter electrode, and a reference electrode, are immersed in a cell having a plating solution to be measured therein. The reference electrode and the working electrode are typically connected to a device for measuring the electrical potential difference between the respective electrodes. The reference electrode generally consists of three components, a half-cell electrode, a half-cell electrolyte, and a reference junction. As used herein, the term "half-cell electrode" generally refers to a solid phase, electron-conducting contact within the half-cell electrolyte, at which contact a half-cell oxidation-reduction reaction occurs that establishes a stable potential between the half-cell electrolyte and the working electrode. Direct physical, and therefore electrical contact between the half-cell electrolyte and the sample plating solution is established through the reference junction, which usually consists of a porous ceramic, glass, or plastic plug (e.g. frit), or other device capable of achieving a fluid mechanical leak having pores large enough to allow equal transport of anions and cations. The reference junction is necessary to establish electrical contact with the plating solution, and therefore, the working electrode. Conventionally, the potential of the working electrode is swept through a voltammetric cycle that includes both a metal plating range and a metal stripping range. The potential of the working electrode is swept through at least two reference baths of non-plating quality, and an additional bath where the quality or concentration of organic additives therein is unknown. In this process, an integrated or peak current used during the metal stripping range may be correlated with the quality of the non-plating bath. As such, the integrated or peak current may be compared to the correlation of the non-plating bath, and the quality of the unknown plating bath determined therefrom. The amount of metal deposited during the metal plating cycle and then re-dissolved into the plating bath during the metal stripping cycle generally correlates to the concentration of particular organics in the plating solution. CVS methods generally observe the total copper ions reduced on an electrode over a predetermined potential range. Inasmuch as accelerators or brighteners counteract the suppressors to increase the plating rate, their quantities may be determined from observation using standard addition or dilution titration techniques.

Generally, measured quantities of additives are injected from the top of the cell into the plating solution using syringes or tubes for testing the plating solution. Unfortunately, as/test volumes may vary from a few milliliters to several hundred milliliters, the cell size must be changed accordingly to accommodate the differing test volumes. Further, as tubes or syringes are used to inject the additives into the plating solutions, it is difficult to accurately inject a microliter or less of the additives into the plating solutions as the volume of the additives must be large enough to be dispensed as a droplet. Micro amounts of additives may be injected by immersing the tube tips into the plating solution. However, residual additives contained within the tubes may diffuse out into the reference bath during the test and contaminate the measurement. Accordingly, due to the potential variation of additives due to the imprecise injections, a plating solution under test may be incorrectly analyzed and therefore cause a plating problem that may affect several batches of substrates affecting the plating throughput, and may ultimately increase the cost of production.

As such, there is a need for an efficient and cost effective apparatus and method for plating solution analysis.

SUMMARY OF THE INVENTION

Embodiments of the invention generally provide an apparatus for analyzing one or more solutions used in a plating process. In one embodiment, the invention provides an apparatus for analyzing plating solutions, wherein the apparatus includes a vessel defining a cavity having a larger volumetric portion adjacent a smaller volumetric portion. Generally, the larger and smaller volumetric portions are adapted to hold solutions. The apparatus further includes a rotating electrode disposed within the cavity, and a fluid injection apparatus coupled to a bottom portion of the vessel adjacent the smaller volumetric region, wherein the fluid injection apparatus is adapted to inject one or more fluids into at least some of the one or more solutions.

In another embodiment, the invention provides an apparatus for analyzing plating solutions used in a substrate plating process. The apparatus includes a vessel defining a cavity adapted to hold the plating solutions, a rotatable working electrode extending at least partially within the cavity, and a motor disposed on top of the vessel and adapted to rotate the working electrode. The apparatus further includes a base coupled to a lower portion of the cavity adjacent a bottom portion of the vessel, wherein the base includes a plurality of fluid ports for coupling fluids from external fluid sources to the cavity. The base further includes a connection member having an upper surface in communication with at least a portion of the cavity, and a fluid junction disposed within the upper surface of the connection member and adapted to combine fluids from the plurality of fluid ports with one or more test solutions. The apparatus further includes a counter electrode disposed parallel to and higher than the working electrode. The apparatus also includes a reference electrode disposed within the base and adapted to couple reference electrolyte fluid to one or more solutions, and a process controller in communication with the system to control the analysis process thereof.

In another embodiment, the invention provides a system for analyzing one or more plating solutions used in a substrate plating process. The system includes a plating cell disposed on a frame having a base thereon. The plating cell includes a conical cavity portion adjacent the base. The base is adapted to couple a plurality of solutions to the plating cell. The system further includes a motor coupled to the plating cell and adapted to rotate a working electrode therein, and a plurality of pumps disposed on the frame and in fluidic communication with the base. The system further includes a heat exchanger disposed on the plating cell and adapted to control temperatures of the one or more plating solutions, and a process controller coupled to at least one of the plating cell, heat exchanger, and pumps, wherein the controller is adapted to control the plating cell, the heat exchanger, and the pumps.

BRIEF DESCRIPTION OF THE DRAWINGS

So that the manner in which the above recited features of the invention are attained can be understood in detail, a more particular description of the invention, briefly summarized above, may be had by reference to the embodiments thereof, which are illustrated in the appended drawings. It is to be noted, however, that the appended drawings illustrate only typical embodiments of this invention, and are therefore, not to be considered limiting of its scope, for the invention may admit to other equally effective embodiments.

DETAILED DESCRIPTION OF THE PREFERRED EMBODIMENT

Figure 1:
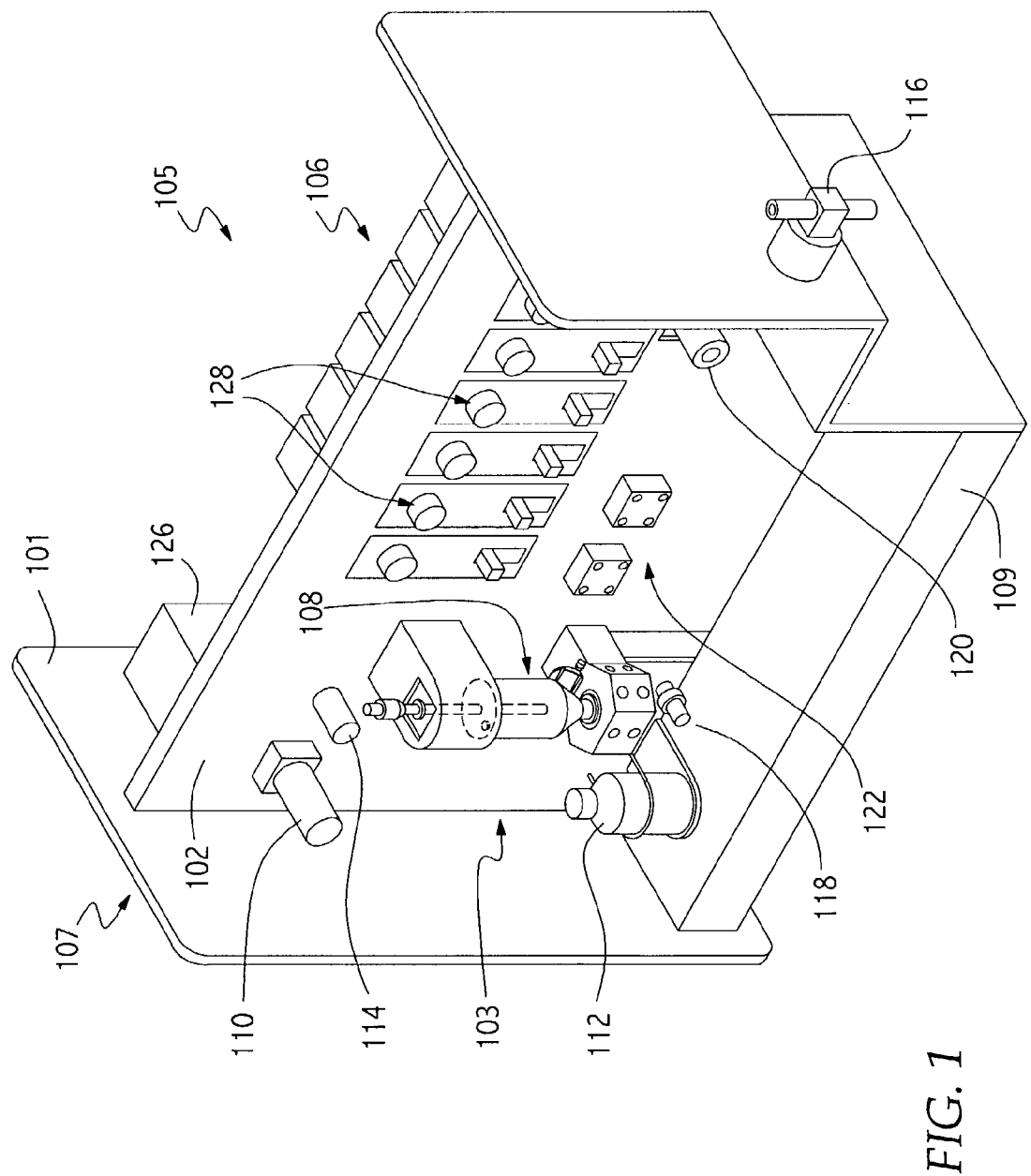
FIG. 1 illustrates a perspective view of one embodiment of a plating solution analysis apparatus for use with aspects of the invention.

FIG. 1 illustrates a perspective view of a plating solution analysis device 105 useful in practicing the invention. In one embodiment, the plating solution analysis device 105 includes a frame 101 that may be divided into functional sections to allow for ease of service and to separate electronic devices from fluids used during testing. The basic sections include a test section 103, a rear electronics section 106, and a grab sample compartment 107. In one aspect, the plating solution analysis device 105 includes a plating cell 108 disposed on the frame 101 within the test section 103. The plating cell 108 is described below with respect to FIG. 2A. In one configuration, the plating solution analysis device 105 may include a reference electrolyte container 112 used to hold electrolytes, such as potassium chloride or other reference electrolytes. A reference electrolyte pump 118 may be adapted to pump reference electrolytes from the reference electrolyte container 112 to the plating cell 108 at the start of the analysis process. The plating solution analysis device 105 may also include a cell water valve 110 adapted to control the flow of water, such as de-ionized water, from external sources (not shown) through a water regulator 116 into the plating cell 108. One or more additive pumps 128 may be disposed on the frame 101 and are adapted to pump solutions, additives, and other testing fluids from external solution containers, such as syringes, through a sample selector valve 120. Plating cell 108 may be fluidly coupled to waste pump/valves 122 disposed on the frame 101 to pump waste fluids therefrom. As illustrated, a potentiostat 126 may be disposed on a wall 102 of the frame 101 to shield the potentiostat from any solution splashing. The potentiostat 126 may be adapted to control the energy input of the plating cell 108.

In one configuration, the plating solution analysis device 105 may be coupled to a data processing system 109. The data processing system 109 may include a computer or other controller adapted to analyze and display input/output signals of the plating solution analysis device 105, and may display the data on an output device such as a computer monitor screen. In general, the data processing system 109 may include a controller, such as programmable logic controller (PLC), computer, or other microprocessor-based controller. The data processing system 109 may include a central processing unit (CPU) in electrical communication with a memory, wherein the memory may contain a plating solution testing program that, when executed by the CPU, provide instructions for controlling the plating solution analysis device 105. The plating solution testing program may use any one of a number of different programming languages. For example, the program code can be written in PLC code (e.g., ladder logic), a higher level language such as C, C++, Java, or a number of other languages. As such, the data processing system 109 may receive inputs from the various components of the plating solution analysis device 105 and generate control signals that may be transmitted to the respective components of the plating solution analysis device 105 for controlling the operation thereof. For example, the data processing system 109 may be configured to control parameters such as the flow rate and the quantity of plating solution dispensed into the plating cell 108, and the timing and quantity of chemicals added to the plating solution by the additive pumps 128.

The plating solution analysis device 105 may utilize a plurality of solutions, additives, and other mixtures during testing of a plating solution. An additive free solution (AFS)

may be used as the main carrier for the additives during testing. For a copper electroplating solution, for example, the AFS can include copper sulfate, sulfuric acid, chloride ions, and other known AFS solutions. The additives, which may be, for example, levelers, suppressors, accelerators, or other additives known in the art, are typically organic materials that adsorb onto the surface of a substrate being plated. Useful suppressors typically include polyethers, such as polyethylene glycol, or other polymers, such as polypropylene oxides, which adsorb on the substrate surface, slowing down copper deposition in the adsorbed sites. Other useful suppressors typically include sodium benzoate and sodium sulfite, which inhibit the rate of copper deposition on the substrate. Useful accelerators typically include sulfides or disulfides, such as bis(3-sulfopropyl) disulfide, which compete with suppressors for adsorption sites, accelerating copper deposition in adsorbed areas.

Figures 2A, 2B:
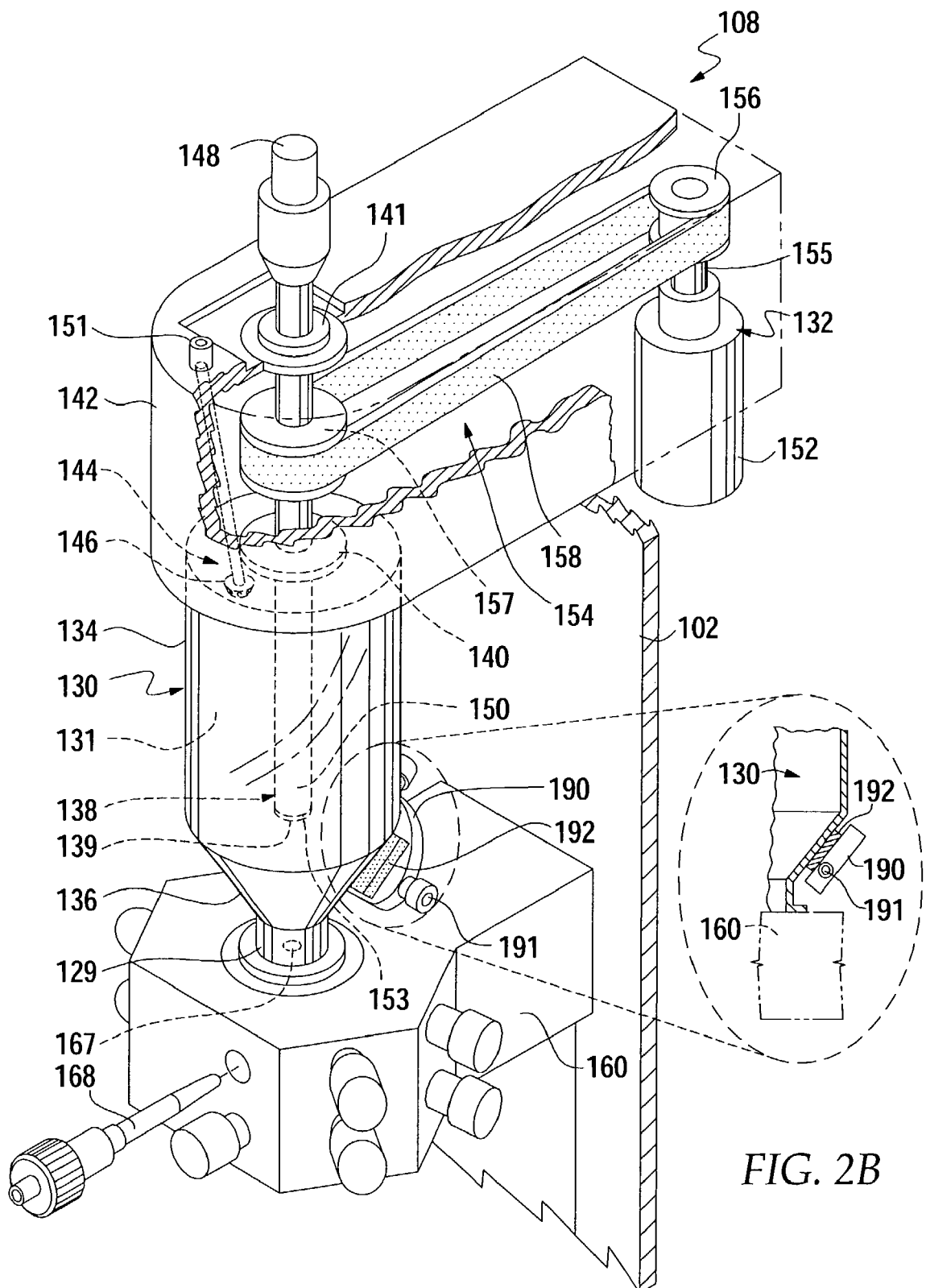
FIG. 2A illustrates a perspective view of one embodiment of a plating cell for use with aspects of the invention.
FIG. 2B illustrates a partial side view of a heat exchanger of FIG. 2A.

FIG. 2A is a perspective view of one embodiment of a plating cell 108. The plating cell 108 includes a vessel 130 supported by a base 160, and coupled to the wall 102. The vessel 130 is adapted to hold one or more plating solutions. As such, to minimize absorption and desorbtion of the plating solution and/or additives from/to the vessel walls, the vessel 130 may be formed from a low porosity material, such as glass or a low porosity plastic. The vessel 130 may be configured to allow external visibility of the one or more plating solutions. To provide an extended volumetric operating range, the shape of the vessel 130 may include a larger top cylindrical section 134 disposed adjacent a smaller conical bottom section 136 forming a cavity 131. Conical section 136 permits a small volume of liquid to be used to reach a tip 139 of a working electrode 138, while the larger cylindrical top section 134 allows larger volumes to be accommodated, such as required for dilutions. For example, the vessel 130 may be configured to analyze test solution volumes from about 20 ml to about 100 ml.

The working electrode 138 may be rotatably disposed in the vessel 130 and adapted to contact at least some of the test plating solution within the cavity 131. The working electrode 138 includes a metal disk 153 disposed on the working electrode tip 139. The metal disk 153 may include corrosive resistant metals, such as platinum and gold, for example, that can be plated and stripped repeatedly without substantial oxidation or dissolution. The metal disk 153 typically has a flat, polished surface between about 2 mm and 7 mm in diameter, and is disposed about flush on the working electrode tip 139. The metal disk 153 is sized at a thickness adapted to sustain one or more plating/stripping processes. The working electrode 138 further includes a rotating electrical contact end 148 distal a solution contact end 150 disposed within the cavity 131. The rotating electrical contact 148 may be configured to allow the working electrode 138 to rotate about its longitudinal axis, while providing a continuous electrical contact with the potentiostat 126 (See FIG. 1). The working electrode 138 is generally mounted in an axial position using a lower and upper bearing 140, 141 axially aligned with the longitudinal axis of the working electrode 138 and disposed within a plating cell cap 142. In one configuration, the plating cell cap 142 is disposed above the larger section 134 of the vessel 130 to allow the working electrode 138 to extend from the plating cell cap 142 though a lid 144. The lid 144 may include a spray nozzle 146 thereon to dispense water within the cavity 131 from a fluid coupling 151.

The plating cell cap 142 includes a motor unit 132. In one aspect, to establish relative motion between the working electrode 138 and the test plating solution, the motor unit 132 includes a motor 152 typically used to rotate the working electrode 138. The rotating working electrode 138 may in effect "stir" the test plating solution to allow a fresh supply of test plating solution to encounter the surface of the working electrode 138. Without such relative motion between the test plating solution and the working electrode 138, the test plating solution becomes depleted at the surface of the working electrode 138 and the deposition rate obtained will not reflect the correct plating rate for the test plating solution. The motor 152 may be positioned within the electronics section 106 (See FIG. 1) to minimize mechanical interference with the plating cell 108 and avoid contact with fluids. To rotate the working electrode 138, a shaft 155 of the motor 152 may be coupled to the working electrode 138 via a drive belt system 154. The drive belt system 154 may include a motor pulley 156 attached to the shaft 155 and an electrode pulley 157 mounted between the lower and upper bearings 140, 141 to the working electrode 138. In one aspect, one or more drive belts 158 couple the motor pulley 156 to the electrode pulley 157 to couple the motor rotation to the working electrode 138. In another aspect of the invention, the motor 152 is adapted to provide a rotational rpm range between about 100 rpm to about 4000 rpm and may be adjusted in incremental rpm steps of about less than about 10 rpm per step. While the motor 152 may be a DC motor, other motor types are contemplated.

Figure 3:
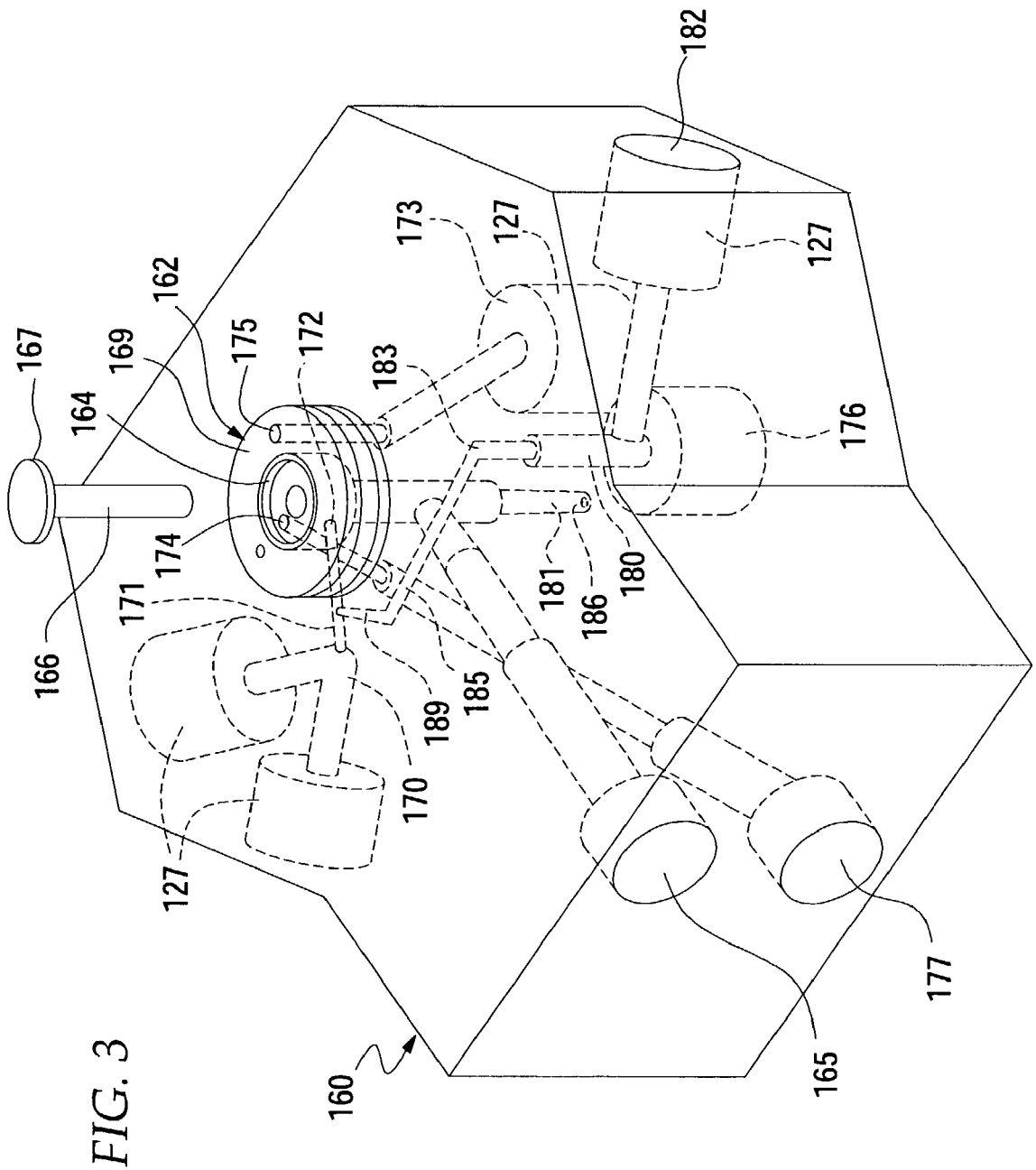
FIG. 3 illustrates a perspective view of one embodiment of a plating cell base.

FIG. 3 is a perspective view of one embodiment of a base 160 used to couple fluids to the vessel 130. FIGS. 1 and 2 are referenced as needed in the discussion of FIG. 3. The base 160 is coupled to the vessel 130 via a connection member 162 adapted to allow the base 160 to be separated from the vessel 130 when needed, such as for example, when being cleaned. While the base connection 162 may be configured as an interference fit, using the friction between a mating connection 129 (See FIG. 2A) in the vessel 130 and the connection member 162 to form a seal therebetween, other types of connections are contemplated such as a threaded connection. In one configuration, the base 160 is formed of a relatively non-porous material such as ceramics, polymers, e.g., Teflon, and other materials employed to minimize absorption and desorbtion of the test plating solution and/or additives from/to surfaces of the base 160 and the connection member 162 in contact therewith.

In one aspect, the base 160 includes a counter electrode receptacle 164 adapted to receive a counter electrode 166. The counter electrode 166 may be slidably disposed within the counter electrode receptacle 164 to allow removal of the counter electrode 166 for cleaning or replacement, for example. The counter electrode 166 further includes a head member 167 distal the counter electrode receptacle 164, and in about axial alignment with the working electrode 138 (see FIG. 2A). In one configuration, the head member 167 may be aligned with the working electrode tip 139 for a more uniform charge distribution, and may be sized somewhat larger than the working electrode area to minimize the current density on the surface of the head member 167. The counter electrode 166 may be formed or plated with materials resistant to corrosion in oxidizing and/or reducing conditions such stainless steel, for example. As the connection member 162 is made of generally pliable material allowing the receptacle diameter to vary under external pressure, the diameter of the counter electrode receptacle 164 may be sized to seal against the edge of the head member 167 when the connection member 162 is compressed when inserted into the mating connection 129. The counter electrode receptacle 164 may include a bore 181 at a distal end. The bore 181 includes an insertion opening 186 to allow the use of a tool, such as a pin, to push on the counter electrode 166 on an end distal head member 167, to easily remove the counter electrode from the counter electrode receptacle 164.

In one configuration, the base 160 includes one or more fluid ports 127 (only four are shown) adapted to couple fluids between the base 160 and external fluid sources and/or storage facilities, such as syringes, and fluid removal systems for waste fluid removal. In one configuration, the fluid ports 127 are adapted to receive external tubing interconnects (not shown) configured to provide a seal between the ports 127 and the external tubing. As shown, two of the fluid ports 127 converge into a fluid hub 170 to combine at least one additive with the AFS to form a test plating solution (e.g., a test solution). Although for clarity only two fluid ports 127 are shown connected to the fluid hub 170, one or more fluid ports 127 may be coupled to the fluid hub 170. The fluid hub 170 is coupled to the vessel 130 through a chamber 171 described below. In one operational aspect, when combining precise small volumes of additives with the AFS, it is important to keep the additives from diffusing or flowing into the AFS or into the test solution until the additives are needed. For this purpose, the fluid ports 127 may be positioned so that the AFS fluid from one fluid port 127 does not flow by density-driven convection into another fluid port 127. In one aspect, this is done by keeping the fluid port 127 coupled to the higher specific gravity fluid lower than the other fluid ports 127. For example, if the AFS has a higher specific gravity relative other fluids, the fluid port 127 supplying the AFS to the fluid hub 170 may be placed lower relative other fluid ports 127 coupled to the other fluids. In another aspect, the fluid paths between fluid ports 127 and hub 170 are angled (i.e., sloped) downward into the more dense solution so that the lighter fluid within it is not exchanged by convention with the solution in the hub 170. In another aspect, the fluid ports 127 may be adapted such that the fluid in the fluid ports 127 may be drawn back into a respective fluid port 127 to form an "air plug" when the one or more fluids are slightly retracted from the fluid hub 170 while it is empty. The air plugs keep the fluids isolated from the transport solution in fluid hub 170 and in turn from the test solution. The chamber 171 may also be sized a sufficient length to prevent diffusion from an additive in the chamber 171 from reaching the test solution contained in the vessel 130 within the time duration of a test. For example, if a test duration where one hour long, the chamber 171 may be sized so that it takes more than one hour for diffusion from an additive to reach the vessel 130. Thus, the fluid ports 127 may be used to control the introduction of fluids into the fluid hub 170, isolate fluids from the test solution, fluidically impede diffusion between the fluids and the AFS, and fluidically impede diffusion of the fluids into the test solution.

In one configuration, the fluid hub 170 may be used to combine fluids to produce mixtures with high dilution ratios. Higher dilution ratios may enable increased measurement precision where small doses of additives or solutions are used. The fluid ports 127 and fluid hub 170 may be used to combine a sample or additive and simultaneously draw the combined mixture from the vessel 130 into a mixing coil (not shown). The mixing coil may be coupled to a fluid port 127, and used to supply the mixture to the vessel 130 during analysis. The mixing coil typically consists of a length of tubing, tightly wound into a coil that may be about five to ten turns long. Drawing solution into and through the mixing coil mixes a combination of fluids, such as is needed for serial dilution. Serial dilution may be done by simultaneously injecting fluids into fluid hub 170 while at about the same time, drawing them out the opposite end of the coil into a reservoir, such as a syringe pump, which is then used to deliver the mixture. Alternatively, the additives and solutions may also be combined by the fluid hub 170, dispensed into the vessel 130, mixed by the rotating action of the working electrode 138, and then drawn back through the fluid hub 170 into a container (not shown) such as a syringe pump to premix a test solution.

To help dislodge air bubbles that may be trapped at the surface of the working electrode tip 139, the chamber 171 couples the fluid hub 170 to a liquid port 172 angled upward and about toward the center of the working electrode tip 139. A test plating solution from the liquid port 172 provides a fluid stream to "sweep" the air bubbles from the electrode tip 139 during the filling of vessel 130. This allows air bubbles to be swept from the downward facing working electrode tip 139. This is in contrast to the conventional top fill approach where air bubbles may be trapped as the solution level rises past the working electrode.

To allow efficient fluid removal after a test, the connection member 162 may be coupled to a fluid waste port 173 using a fluid exit port 175 disposed on surface 169 of connection member 162. The fluid exit port 175 may be configured to rapidly flush waste solutions when required. The fluid exit port 175 may have an oblong cross section adapted to allow sufficient liquid surface tension to keep the test plating solutions from escaping during a testing process, while having a cross-sectional area sized to allow rapid removal of the testing solutions when desired though the fluid waste port 173.

The base 160 may include a plurality of electrical connections to provide stimulation signals to and from the base 160 and controller 109. An electrical connection port 165 is adapted to receive electric signals, such as current from a potentiostat 126 (See FIG. 1), to power the counter electrode 166. A replaceable contact pin 168 (See FIG. 2A), illustrated in a disconnected position, when in contact with the counter electrode 166, conducts an electric bias to the counter electrode 166 from an external source (not shown). It is contemplated that the contact pin 168 may be spring-loaded to urge the contact pin 168 against the counter electrode 166 to provide lower electrical contact resistance. The base 160 may also include a reference electrode port 176 adapted to conduct reference current to a connecting wire described below with reference to FIG. 4 described below.

A thermal sensor 174, such as a thermistor or other thermal detection device, may be disposed in thermal contact with the counter electrode 166 to provide a temperature measure of the plating solution being tested. The thermal sensor 174 may be positioned proximate the underside of the head member 167 to provide improved thermal conduction with the test plating solution. The thermal sensor 174 may be coupled to an external temperature sensor circuit (not shown) using the temperature sensor port 177.

Figure 4:
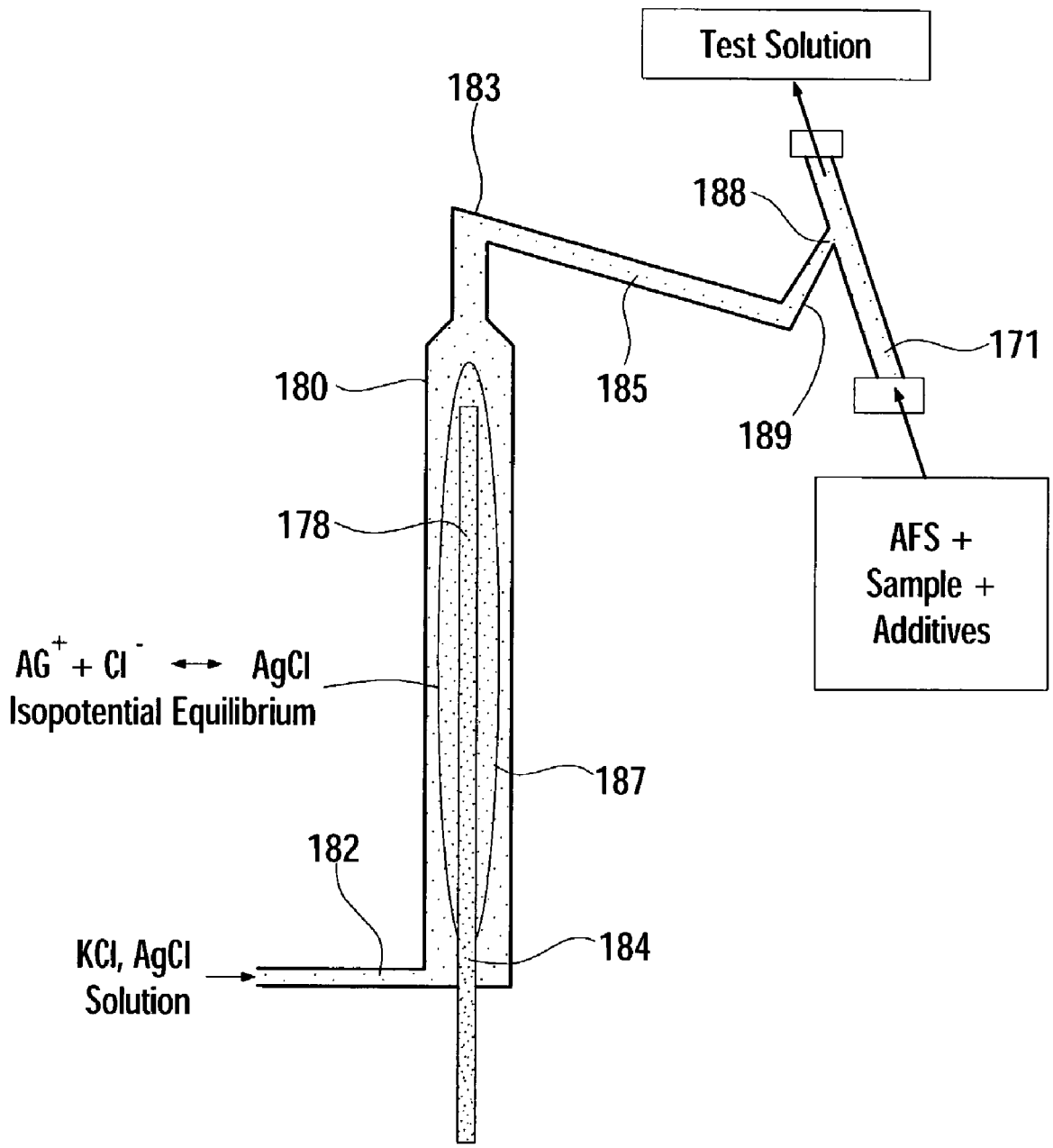
FIG. 4 illustrates a diagrammatic view of one embodiment of a reference electrode configuration for use with aspects of the invention.

With reference to FIGS. 3 and 4, the base 160 may also include a reference electrode port 176 to receive a reference electrode 178. The reference electrode 178 may be a saturated Calomel reference wire electrode (SCE) or silver lined with silver chloride, for example. In one configuration, the reference electrode 178 may be formed from a connecting wire 184, such as a silver/silver chloride wire having a silver chloride layer 187 thereon. The connecting wire 184 is connected to a potentiostat 126 (See FIG. 1), through the reference electrode port 176. The potentiostat 126 keeps the voltage between the working electrode tip 139 and the reference electrode 178 constantly proportional to a signal from controller 109. The potentiostat 126 accomplishes this by varying current between the counter electrode 166 and working electrode tip 139. In another mode, the potentiostat 126 is switched to work as a galvonostat where the current between the counter electrode 166 and the working electrode tip 139, is kept proportional to a signal from the controller 109. In this mode, the voltage potential between the working electrode tip 139 and reference electrode 178 is recorded by the controller 109.

As illustrated in FIG. 4, the reference electrode 178 may be disposed in a reference electrode chamber 180. The reference electrode chamber 180 is coupled on one end to a reference solution port 182, and on an opposing end 183 to a z-shaped chamber 185. The z-shaped chamber 185 couples reference solutions (i.e., conductive salt solutions) from the reference electrode chamber 180 to the chamber 171 through a reference fluid junction 188. Sections of the z-shaped chamber 185 may be inclined to prevent density-driven fluid exchange between the reference solution and the test plating solution within the chamber 171 to minimize cross-contamination. The chamber 171 may be sized to increase the diffusion time of the electrolyte salts to minimize the effects of diffusion. The z-shaped chamber 185 may also include a constricted section 189 sized to impede the reference solution and test plating solution exchange. The reference fluid junction 188 is sized to allow communication between the reference solution and the testing solution and to prevent changing junction potential due to clogging. During testing, to minimize the reference solution contamination with the test plating solution, while allowing the reference solution and test plating solution to make electrical contact, the reference solution flow is stopped within the reference electrode chamber 180 and the z-shaped chamber 185 to form a conductive slug between the electrode chamber 180 and testing solution. In another configuration, the reference solution is delivered at a lower end of the reference electrode 178 from the reference solution port 182 and is pumped vertically about the reference electrode 178 to assist in the entrainment and removal of air bubbles. In an alternative configuration, the chamber 185 may be coupled to the fluid exit port 175 to combine the reference solution with a test plating solution therein. This isolates the reference solution from the test plating solution in the vessel 130, particularly to stirred solutions within the vessel 130, while preventing diffused electrolyte salts from being carried into the test plating solution during the addition of additive doses.

Figure 5A:
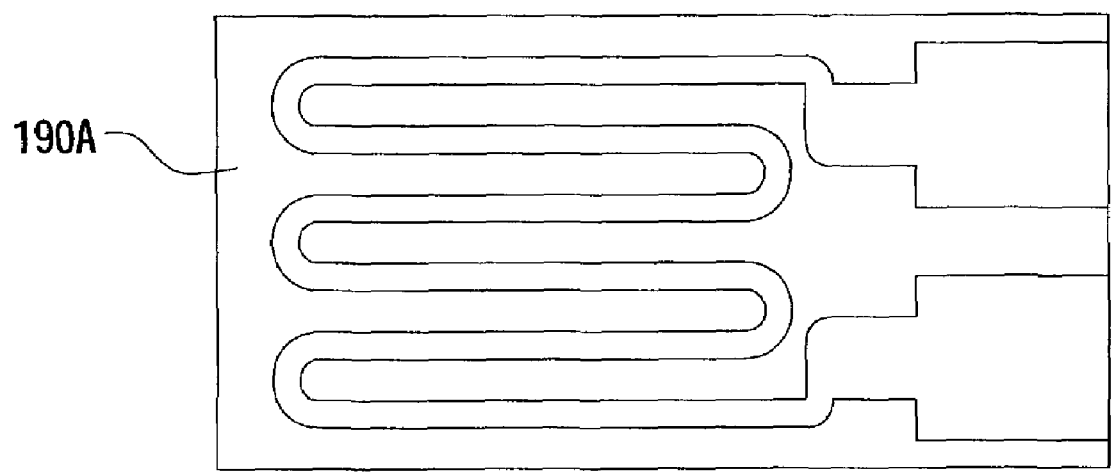
FIGS. 5A and 5B illustrate a simplified view of one embodiment of a heat exchanger used with aspects of the invention.
Figure 5B:
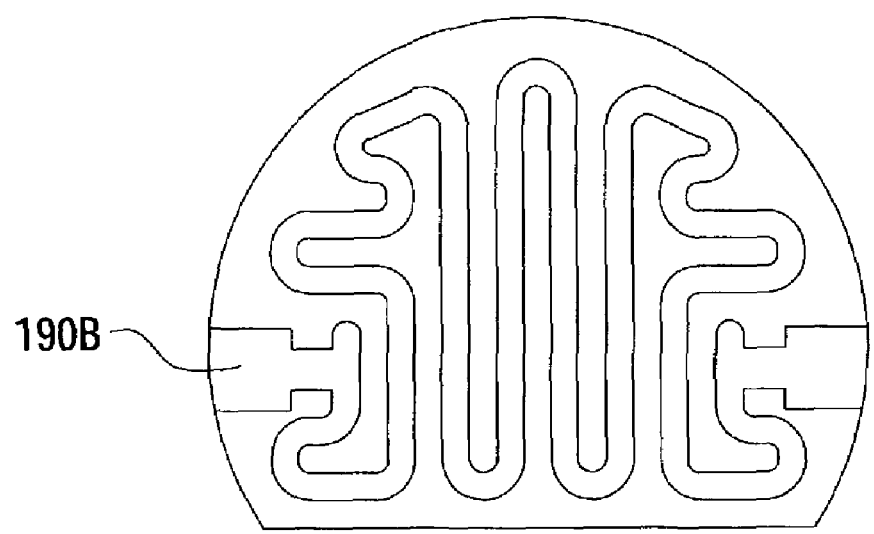

In order to maintain a desired temperature of a test plating solution, a heat exchanger 190 and thermoelectric module 192 may be disposed in thermal contact with the vessel 130 as illustrated in FIGS. 2A and 2B. For improved thermal contact, the thermoelectric module 192 may be disposed in contact with a flat area of the vessel 130. The heat exchanger 190 may generally include a coolant input 191 to accept coolant from a coolant valve 114 (see FIG. 1). In one aspect, as illustrated in FIG. 2B, the heat exchanger 190 includes one or more of the thermoelectric modules 192 sandwiched between the heat exchanger 190 and the vessel 130 to allow the test plating solution to be brought above, and below, ambient temperature. FIGS. 5A and 5B illustrate two embodiments 190A and 190B of heat exchanger 190. Heat exchangers 190A and 190B reflect trade offs between lower cost and a more compact design, respectively. In one configuration, the process controller 109 controls the thermoelectric module 192 in a loop process using the thermal data derived from the thermal sensor 174 to maintain a desired test plating solution temperature.

Figure 6:
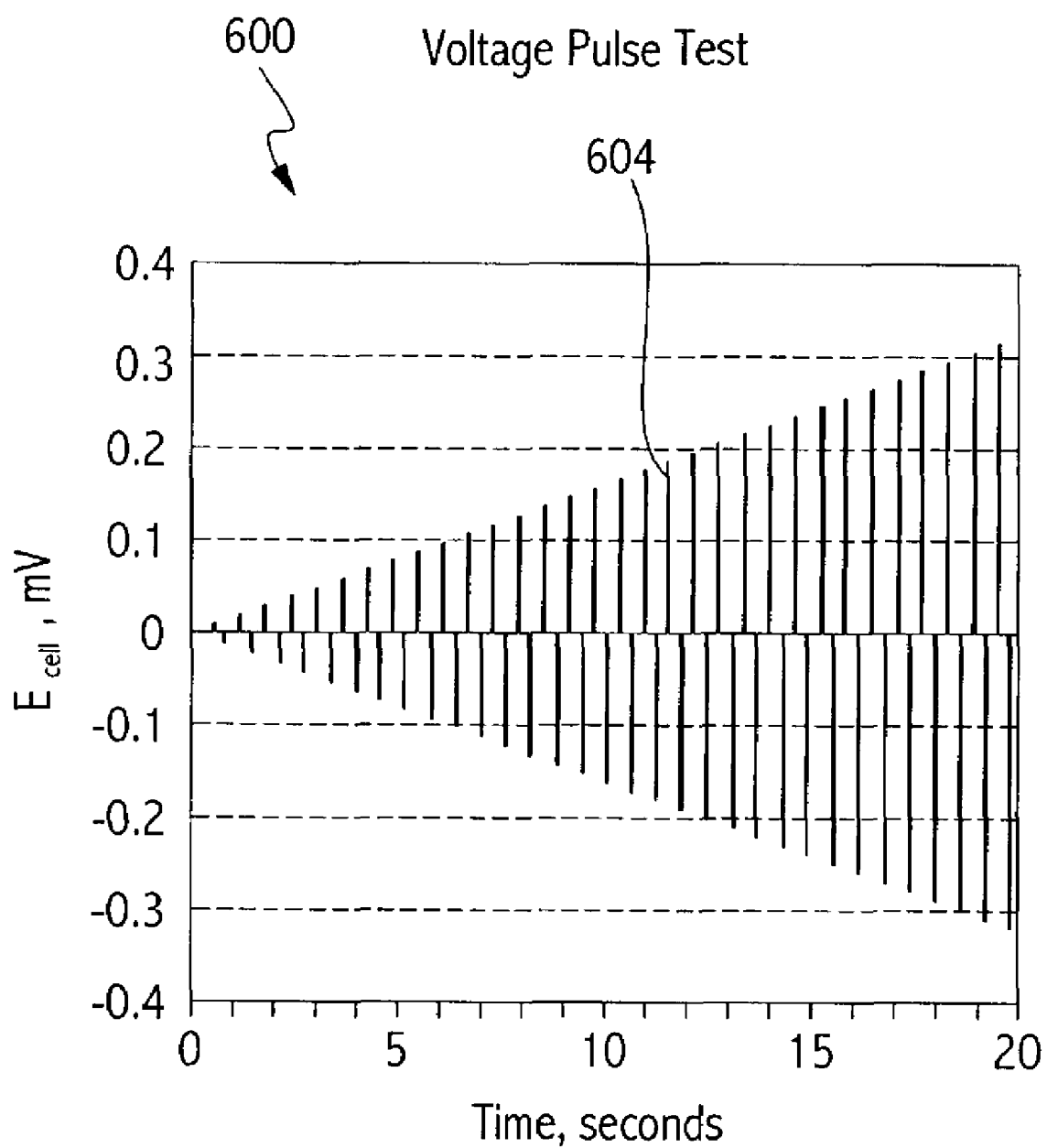
FIG. 6 illustrates one type of stimulation waveform for use with aspects of the invention.

Embodiments of the invention further provide cyclic or pulse voltammetric methods for measuring the concentration of additives in a plating solution. The methods generally include pumping electrolyte solution from the reference electrolyte pump 118 into the reference electrode chamber 180 and z-shaped chamber 185. The vessel 130 is cleaned and a carrier solution (e.g., AFS) along with the sample of the plating solution, and one or more additives, is pumped from the fluid ports 127 through the fluid hub 170 and through the liquid port 172 to form a test solution in the vessel 130. A small volume of additives may be added (e.g., 5 micoliters) before the addition of a carrier solution, which is subsequently added to flush the additive into the vessel 130 to create a liquid plug, or gap within the chamber 171. The liquid plug isolates the additive supply from the test plating solution, thus preventing diffusion of the additive from altering test results during testing. The methods further include cycling the potential of the working electrode 138 through a series of steps while measuring current to determine the amount of additives present. The methods also includes steps such as a stripping, cleaning, pre-plating, equilibration, and metal deposition step. For example, the metal stripping step includes pulsing a potential between the working electrode 138 and the reference electrode 178 between an initial voltage and a metal stripping potential, until the corresponding stripping current is approximately 0 mA/cm. As used herein, the term "pulse" refers to immediately applying a desired potential from a prior potential. Next, the potential is pulsed between an initial potential and a cleaning potential to clean the working electrode 138 in the cleaning step. A thin layer of metal is then plated onto the surface of the working electrode 138 in a pre-plating step by pulsing to a pre-plating potential. The potential is then pulsed back to the initial potential in an equilibration stage. The final step is a metal deposition step. The deposition step includes scanning to an additive sensitive potential, i.e., a potential where the additive desorbs from the working electrode, holding the additive sensitive potential, and reversing the potential and scanning back to the open circuit potential. As used herein, the term "scanning" refers to either linear or pulsed ramping to a desired potential from a prior potential. The additive sensitive potential may vary and is dependent on the additive to be measured. FIG. 6 illustrates one example of a pulsed ramp waveform 600 used to perform voltammetric organic analysis of a test plating solution with the plating solution analysis device 105. The waveform 600 includes a plurality of anodic and cathodic pulses adapted to provide either a controlled current or potential to the working electrode 138. In one aspect, the waveform 600 is formed from a plurality of varying pulses 604 that correspond to a range of working electrode current or potential.

While the foregoing is directed to embodiments of the invention, other and further embodiments of the invention may be devised without departing from the basic scope thereof, and the scope thereof is determined by the claims that follow.

What is claimed is:

1. An apparatus for analyzing one or more solutions used in a plating process, comprising:

a vessel defining a cavity having a larger volumetric portion adjacent a smaller volumetric portion, wherein the larger and smaller volumetric portions are adapted to hold the one or more solutions therein;

a rotating electrode disposed within the cavity and positioned within at least a portion of the larger and smaller volumetric portions; and a fluid injection apparatus coupled to a bottom portion of the vessel adjacent the smaller volumetric region, wherein the fluid injection apparatus is adapted to inject one or more fluids into at least one of the larger or smaller volumetric portions, and wherein the fluid injection apparatus comprises a reference electrode disposed within a reference electrode chamber coupled to an access port in fluidic communication with the one or more solutions.

2. The apparatus of claim 1, wherein a cross-section of the smaller volumetric region is generally conical and tapers from the larger volumetric portion to the fluid injection apparatus.

3. The apparatus of claim 1, wherein the smaller volumetric portion is coupled to the fluid injection apparatus by a low-porosity connector selected from plastic, glass, and combinations thereof, adapted to minimize absorption and desorption of organic compounds into the one or more solutions.

4. The apparatus of claim 1, further comprising a heat exchanger disposed on the vessel and adapted to control the temperature of the one or more solutions therein.

5. The apparatus of claim 1, wherein the fluid injection apparatus comprises a thermal sensor in thermal communication with the one or more solutions.

6. The apparatus of claim 1, further comprising a counter electrode in fluidic communication with the one or more solutions.

7. The apparatus of claim 1, wherein the fluid injection apparatus comprises a fluid hub configured to receive the one or more fluids from one or more fluid sources coupled to one or more fluid delivery paths, wherein the fluid hub is configured to combine the one or more fluids into a resultant solution.

8. The apparatus of claim 7, wherein the fluid hub is configured to allow the one or more fluids to be isolated from the solution.

9. The apparatus of claim 7, wherein the fluid hub includes a chamber coupled to the vessel, wherein the chamber is sized to extend diffusion time of the one or more fluids into the vessel.

10. The apparatus of claim 7, wherein the one or more fluid delivery paths are positioned to prevent density-driven convection between the fluids and the solution.

11. The apparatus of claim 7, wherein the one or more fluid delivery paths include a sloping path coupled to a fluid source, wherein the sloping path is angled to prevent density-driven fluid exchange between the fluid hub and the fluid source.

12. The apparatus of claim 7, wherein the one or more fluid delivery paths are adapted to hold an air plug when analyzing the one or more solutions to isolate the one or more fluids from the fluid hub.

13. The apparatus of claim 7, wherein the one or more fluid delivery paths include a chamber coupled to the cavity, wherein the chamber is configured to hold a liquid plug used to isolate an electrolyte solution disposed within the reference electrode chamber from the resulting solution.

14. An apparatus for analyzing one or more solutions used in a plating process, comprising:
a vessel defining a cavity having a larger volumetric portion adjacent a smaller volumetric portion, wherein the larger and smaller volumetric portions are adapted to hold the one or more solutions therein;
a rotating electrode disposed within the cavity and positioned within at least a portion of the larger and smaller volumetric portions; and
a fluid injection apparatus coupled to a bottom portion of the vessel adjacent the smaller volumetric region, wherein the fluid injection apparatus is adapted to inject one or more fluids into at least one of the larger or smaller volumetric portions, and wherein the fluid injection apparatus comprises a fluid exit port having an oblong cross-section configured to prevent the migration of the one or more solutions during a testing process into a fluid waste portal.

15. An apparatus for analyzing one or more plating solutions used in a substrate plating process, comprising;
a vessel defining a cavity adapted to hold the one or more plating solutions therein;
a rotatable working electrode extending at least partially within the cavity;
a motor disposed on top of the vessel and adapted to rotate the working electrode;
a base coupled to a lower volumetric portion of the cavity adjacent a bottom of the vessel, wherein the base includes a plurality of fluid ports for coupling fluids from external fluid sources to the cavity, the base further includes a connection member having an upper surface in communication with at least a portion of the cavity;
a fluid junction disposed within the upper surface of the connection member and adapted to combine fluids from the plurality of fluid ports with one or more test solutions;
a counter electrode disposed in the base, wherein the counter electrode is larger than and in about axial alignment with the working electrode;
a reference electrode disposed within the base and adapted to couple reference electrolyte fluid to the one or more solutions; and
a process controller in communication with the system to control the analysis process thereof.

16. The apparatus of claim 15, further comprising at least one pump adapted to pump the one or more solutions to and from the cavity.

17. The apparatus of claim 15, further comprising a thermo-electric heat module adapted to raise and lower a temperature of the one or more solutions about an ambient temperature.

18. The apparatus of claim 15, wherein the cavity tapers from a larger upper volume to a lower smaller volume.

19. The apparatus of claim 15, wherein the vessel comprises glass, ceramics, polymers, or combinations thereof.

20. The apparatus of claim 15, wherein the base comprises ceramics, polymers, or combinations thereof.

21. The apparatus of claim 15, wherein the base further comprises a plurality of electrical signal ports adapted to couple electrical signals to and from the base.

22. The apparatus of claim 21, wherein the electrical signals comprise a counter electrode stimulation signal, a reference electrode signal, a thermal data signal, or combinations thereof.

23. The apparatus of claim 15, wherein the fluid junction comprises an angled section about axially aligned with respect to the counter electrode, wherein the angled section is positioned to direct at least some of the one or more solutions toward the counter electrode to dislodge air bubbles therefrom.

24. The apparatus of claim 15, wherein the base includes a reference electrode chamber coupled to a z-shaped section having a cross-section configured to minimize fluidic contamination between the one or more test solutions and the reference electrolyte fluid.

25. The apparatus of claim 24, wherein the z-shaped section is positioned substantially horizontal with respect to the longitudinal axis of the reference electrode chamber and further comprises a tapered end coupled to the fluid junction and adapted to minimize electrolyte leakage into the cavity.

* * * * *

UNITED STATES PATENT AND TRADEMARK OFFICE
CERTIFICATE OF CORRECTION

PATENT NO.        : 6,986,835 B2
APPLICATION NO. : 10/287901
DATED             : January 17, 2006
INVENTOR(S)       : Todd Alan Balisky, Donald A. Cameron and Zhi-Wen Sun It is certified that error appears in the above-identified patent and that said Letters Patent is hereby corrected as shown below:

In the Specification

Column 2, Line 32: Change "as/test" to --as test--

Column 7, Line 46: Change "where" to --were--

Column 10, Line 8: Change "micoliters" to --microliters--

Signed and Sealed this

First Day of August, 2006

JON W. DUDAS
*Director of the United States Patent and Trademark Office*